United States Patent [19]

Nierth et al.

[11] Patent Number: 4,739,117

[45] Date of Patent: Apr. 19, 1988

[54] PROCESS FOR THE ISOLATION OF DIARYL GUANIDINES

[75] Inventors: Alfred Nierth, Dormagen; Bernhard Scherhag, Leverkusen; Reinhard Preuss, Dormagen; Heinz Klose; Salvatore Sabia, both of Cologne, all of Fed. Rep. of Germany

[73] Assignee: Bayer Aktiengesellschaft, Leverkusen, Fed. Rep. of Germany

[21] Appl. No.: 942,153

[22] Filed: Dec. 16, 1986

[30] Foreign Application Priority Data

Dec. 18, 1985 [DE] Fed. Rep. of Germany ....... 3544730

[51] Int. Cl.$^4$ ........................................... C07C 129/12
[52] U.S. Cl. .................................................. 564/238
[58] Field of Search ........................................ 564/238

[56] References Cited

U.S. PATENT DOCUMENTS 1,884,509 10/1932 Bailey ................................. 564/238
1,897,220 2/1933 Ter Horst .

Primary Examiner—Donald B. Moyer
Assistant Examiner—L. Hendriksen
Attorney, Agent, or Firm—Sprung Horn Kramer & Woods

[57] ABSTRACT

Diaryl guanidines can be obtained in a high degree of purity and in high yields from the crude melt obtained from the reaction of arylamines and cyanogen chloride by dissolving the hot melt in water, extracting this solution with a mixture of at least one water insoluble, apolar hydrocarbon and at least one polar organic compound and precipitating the diaryl guanidine from the purified, aqueous solution by the addition of alkali metal hydroxide.

12 Claims, No Drawings

PROCESS FOR THE ISOLATION OF DIARYL GUANIDINES

This invention relates to a process for isolating diaryl guanidines in a highly pure state and in high yields.

In the continuous industrial production of diaryl guanidines from aniline, toluidines or xylidines and cyanogen chloride, the reaction product is obtained in the form of a dark melt consisting of the hydrochloride of the corresponding diaryl guanidine and unwanted by-products which interfere with further working up to the pure diaryl guanidine (DE-AS 1,518,818).

The melt has hitherto been purified by dissolving it in water and precipitating the free diaryl guanidine from the acid diaryl guanidine hydrochloride solution by the addition of an alkali liquor.

The diaryl guanidine obtained by this method is, however, coloured and tends to form smears due to the presence of residues of unreacted amine and by-products of the synthesis which are precipitated at the same time.

For further purification, active charcoal is added to the diaryl guanidine hydrochloride solution which is then filtered after the charcoal has had some time to act on the solution (U.S. Pat. No. 1,727,060). Although this method is effective, it is uneconomical.

It is also known (U.S. Pat. Nos. 1,897,220; 1,884,509) to treat the aqueous solution of diaryl guanidines with water insoluble, apolar hydrocarbons so that the hydrophobic constituents of the impurities can be partly removed, but the aminic impurities which are also present in a diaryl guanidine hydrochloride solution in the form of hydrochlorides and are insoluble in apolar solvents cannot be removed by this method.

The use of hydrophilic solvents is generally unsuitable owing to the considerable solubility of these solvents in the aqueous guanidine hydrochloride solution and conversely the solubility of the guanidine hydrochloride solution in the solvent, as this leads to considerable losses of solvent and of guanidine.

It has now been found that diaryl guanidines can be obtained in high yields and with a high degree of purity from crude, solvent-free diaryl guanidine hydrochloride melts by dissolving the hot melts in water, extracting the resulting solution with a mixture of at least one apolar, water insoluble hydrocarbon and at least one polar organic compound, and precipitating the pure diaryl guanidines from the purified aqueous solution by the addition of an alkali metal hydroxide.

Suitable water insoluble, apolar solvents include in particular aliphatic, cycloaliphatic and aromatic hydrocarbons boiling at temperatures from 80° to 200° C. Toluene, o-, m- and p-xylene, ethylbenzene and isopropyl benzene are preferred.

Aliphatic and cyclo-aliphatic alcohols containing 3 to 10 carbon atoms and aromatic nitriles such as benzonitrile and tolunitrile are suitable polar extracting agents.

Mixtures of water insoluble hydrocarbons and mixtures of polar extracting agents may also be used according to the invention. The proportions in which polar solvents are mixed with apolar solvents may vary within wide limits but the solvent mixture preferably contains 5 to 40% by weight of polar compound, most preferably 5 to 20% by weight.

The use of $C_3$–$C_{10}$ alcohols with toluene or xylene has the advantage that the phases can easily be separated after extraction.

Another advantage of the process according to the invention is that the extraction system can be adjusted to the required degree of purification of the crude guanidine hydrochloride solution. Thus if streams of substances are fed at a constant rate into the extraction apparatus, a uniformly pure diaryl guanidine may be obtained simply by varying the proportions of polar to apolar solvents even if the quality of the crude solution fluctuates.

The process may be carried out batch-wise or continuously. A continuous process in which the solvent mixture is also continuously freed from the extracted by-products and returned to the process is preferred.

The process is preferably carried out at 20° to 100° C. and at pH 5.0 to 7.0.

The proportion by weight of crude melt to water is preferably in the range of 1:3 to 1:20, most preferably from 1:4 to 1:10.

The proportion by weight of organic solvent to water is preferably in the range of 1:5 to 1:20, most preferably from 1:7 to 1:14.

EXAMPLE 1

(a) 50 g of a crude melt of diphenyl guanidine hydrochloride obtained from the reaction of aniline and cyanogen chloride (DE-AS 1,518,818) and heated to about 160° C. were stirred into 280 g of hot water.

A brown, aqueous solution formed, but it still contained undissolved constituents.

This solution was cooled to 60° C. with stirring and 30 g of a mixture of 10% by weight of hexanol-1 and 90% by weight of o-xylene were added.

After adjustment of the pH to 6.4 with sodium hydroxide solution, the stirrer was stopped. The phases separated immediately. The aqueous phase was removed and again extracted with 30 g of the above mentioned extraction solution at pH 6.4. Colourless diphenyl guanidine was then precipitated by the addition of sodium hydroxide solution to adjust the pH to 11.8. The precipitate was washed with water and dried. The yield amounted to 93.2% of the theoretical yield. Volumetric analysis by titration showed that the precipitate contained 99.1% of product having a melting point of 149.5° C.

(b) For comparison, 50 g of the same crude melt were dissolved in 280 g of hot water. The diphenyl guanidine was precipitated from the solution by the addition of sodium hydroxide solution to adjust the pH to 11.8. The beige coloured product obtained was washed with water and dried. The yield was 98.3% of the theoretical yield.

Active substance content, (determined by titration): 98.1%

Melting range: 143.1°–145.4° C.

Colour: Beige

EXAMPLE 2

(a) 50 g of the heated crude melt were dissolved in 280 g of hot water. The aqueous solution was cooled and extracted twice with 20 g of a mixture of 10% by weight of benzonitrile and 90% by weight of toluene. The pH was adjusted to 6.2 with sodium hydroxide solution. After separation of the phases, the aqueous solution was steam distilled and the diphenyl guanidine was then precipitated by the addition of sodium hydroxide solution. The product was colourless and had a melting point of 146.8° C. The yield amounted to 94.1% of the theoretical yield.

EXAMPLE 3

(a) In a continuous experiment, an approximately 30% by weight aqueous crude diphenyl guanidine hydrochloride solution was diluted to 12% by weight by the addition of water and tempered in a buffer vessel at 60° C. 50 liters per hour of the diluted aqueous solution were then continuously extracted in counter current with 5 liters per hour of a mixture of 95% by weight of o-xylene and 5% by weight of hexanol.

The pH was adjusted to 6.9 by the simultaneous addition of sodium hydroxide solution. The experiment was carried out in a 2-stage mixer and separator battery. The aqueous solution discharged from the apparatus was analytically examined at regular intervals.
Melting point: 147.6° C.
Content of active substance (determined by titration): 98.5%
The yield amounted to 92.9% of the theoretical yield.

(b) In a parallel experiment, a sample was removed from the crude diphenyl guanidine hydrochloride solution and its quality determined on the isolated product which was obtained by stirring sodium hydroxide into the solution to adjust the pH to 11.8. The melting range was 141.1° to 144.3° C. The colour of the product was yellow. The yield amounted to 98.1% of the theoretical yield.

We claim:

1. A process for the isolation of diaryl guanidines from a crude melt obtained from the reaction of arylamines and cyanogen chloride, comprising dissolving the hot melt in water, extracting the solution obtained with a mixture of at least one water insoluble, apolar hydrocarbon solvent and at least one polar organic compound, and precipitating the diaryl guanidine from the purified, aqueous solution by the addition of alkali metal hydroxide.

2. A process according to claim 1, wherein the apolar, water insoluble solvents are selected from the group consisting of aliphatic, cycloaliphatic and aromatic hydrocarbons having boiling points in the range of 80° C. to 200° C.

3. A process according to claim 1, wherein the polar extracting agents are selected from the group consisting of aliphatic and cycloaliphatic alcohols having 3 to 10 carbon atoms and aromatic nitriles.

4. A process to claim 1, wherein the extraction is carried out a temperatures in the range of 20° C. to 100° C.

5. A process according to claim 1, wherein the extraction is carried out in a pH range of 5.0 to 7.0.

6. A process according to claim 1, wherein the solvent mixture contains 5 to 40% by weight of the polar compound.

7. A process according to claim 1, wherein the proportion by weight of the crude melt to water is in the range of 1:3 to 1:20.

8. A process according to claim 1, wherein the proportion by weight of the organic solvent to water is in the range of 1:5 to 1:20.

9. A process according to claim 1, wherein the solvent is selected from the group consisting of toluene, o-xylene, m-xylene, p-xylene, ethylene benzene and isopropyl benzene.

10. A process according to claim 1, wherein the polar extracting agent is selected from the group consisting of benzonitrile and tolunitrile.

11. A process according to claim 1, wherein the proportion by weight of the crude melt to water is 1:4 to 1:10.

12. A process according to claim 1, wherein the proportion by weight of the organic solvent to water is 1:7 to 1:14.

* * * * *